(12) United States Patent
Argentine

(10) Patent No.: US 9,629,620 B2
(45) Date of Patent: Apr. 25, 2017

(54) METHOD AND APPARATUS FOR FORMING A SUTURE CONNECTOR IN SITU

(71) Applicant: Medtronic Vascular, Inc., Santa Rosa, CA (US)

(72) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 416 days.

(21) Appl. No.: 14/180,016

(22) Filed: Feb. 13, 2014

(65) Prior Publication Data

US 2015/0223799 A1 Aug. 13, 2015

(51) Int. Cl.
*A61B 17/04* (2006.01)
*A61B 17/00* (2006.01)

(52) U.S. Cl.
CPC ...... *A61B 17/0401* (2013.01); *A61B 17/0467* (2013.01); *A61B 17/0487* (2013.01); *A61B 2017/00862* (2013.01); *A61B 2017/0409* (2013.01); *A61B 2017/0488* (2013.01)

(58) Field of Classification Search
CPC ........ A61B 17/0401; A61B 2017/0488; A61B 17/0487; A61B 2017/0409; A61B 17/0485; A61B 17/0467
See application file for complete search history.

(56) References Cited

U.S. PATENT DOCUMENTS

| | | | |
|---|---|---|---|
| 3,989,049 A | 11/1976 | Yoon | |
| 5,931,844 A | 8/1999 | Thompson et al. | |
| 5,948,001 A | 9/1999 | Larsen | |
| 6,117,144 A | 9/2000 | Nobles et al. | |
| 6,562,052 B2 | 5/2003 | Nobles et al. | |
| 7,803,167 B2 | 9/2010 | Nobles et al. | |
| 8,197,497 B2 | 6/2012 | Nobles et al. | |
| 8,469,975 B2 | 6/2013 | Nobles et al. | |
| 2006/0200199 A1* | 9/2006 | Bonutti ............. A61B 17/0487 606/232 |
| 2007/0010829 A1* | 1/2007 | Nobles ............... A61B 17/0485 606/148 |

(Continued)

OTHER PUBLICATIONS

PCT/US2015/011519 International Search Report and the Written Opinion, mailed Apr. 8, 2015.

(Continued)

*Primary Examiner* — Thomas McEvoy

(57) ABSTRACT

A system for forming a suture connector in situ includes a suture connector placement device having a handle, an outer shaft, an intermediate shaft, and a push rod, and a suture connector having a sleeve and a plug. The intermediate shaft is slidingly disposed through a lumen of the outer shaft, and the push rod is slidingly disposed through a lumen of the intermediate shaft. When the suture connector is in a loaded configuration within the suture connector placement device, the sleeve is radially disposed between the intermediate shaft and the outer shaft and the plug is positioned proximal to the sleeve within the lumen of the intermediate shaft. Distal advancement of the push rod moves the plug into the sleeve and proximal retraction of the intermediate shaft releases the resilient sleeve onto the plug, thereby securing two suture portions between the sleeve and the plug.

20 Claims, 17 Drawing Sheets

(56) References Cited

U.S. PATENT DOCUMENTS

2010/0121349 A1\*  5/2010  Meier ................ A61B 17/0467
                                                    606/139
2010/0256679 A1   10/2010  Ducharme
2013/0158600 A1    6/2013  Conklin et al.

OTHER PUBLICATIONS

U.S. Appl. No. 13/802,551, filed Mar. 13, 2013, Argentine.
U.S. Appl. No. 13/802,563, filed Mar. 13, 2013, Argentine.

\* cited by examiner

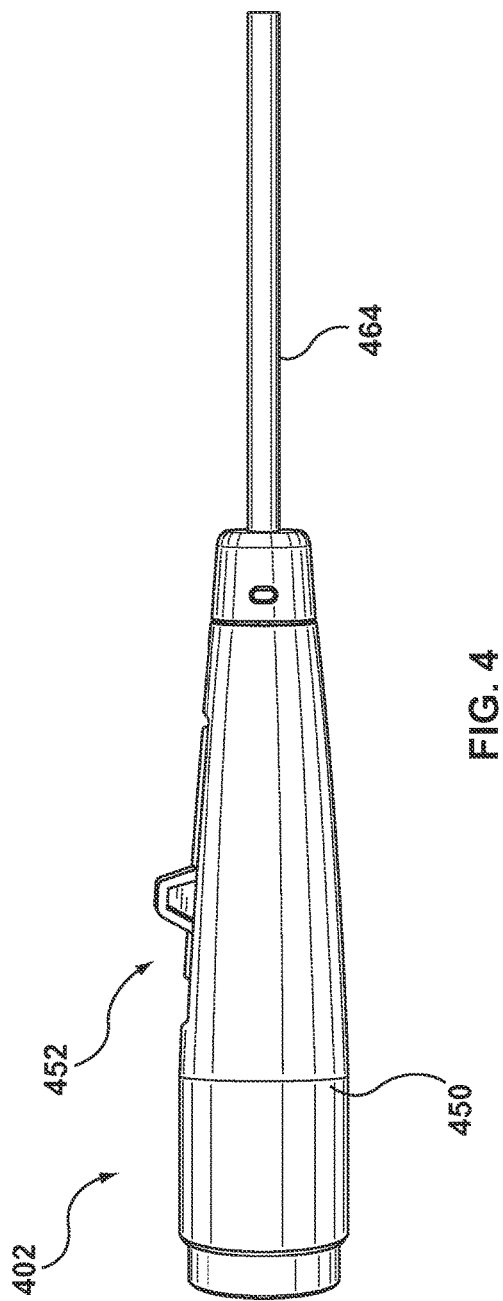
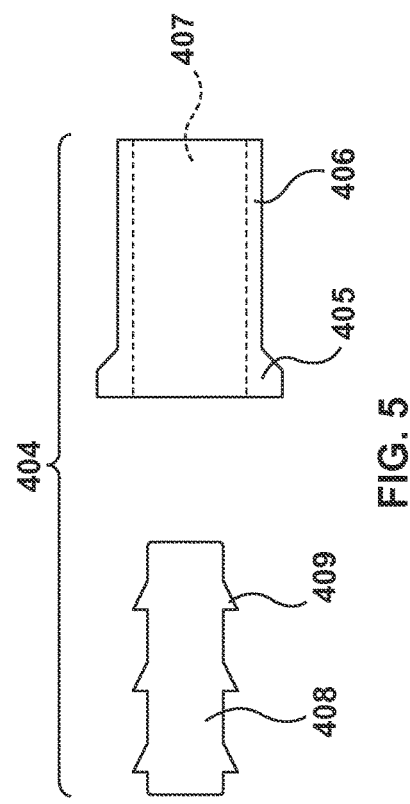
FIG. 4
FIG. 5

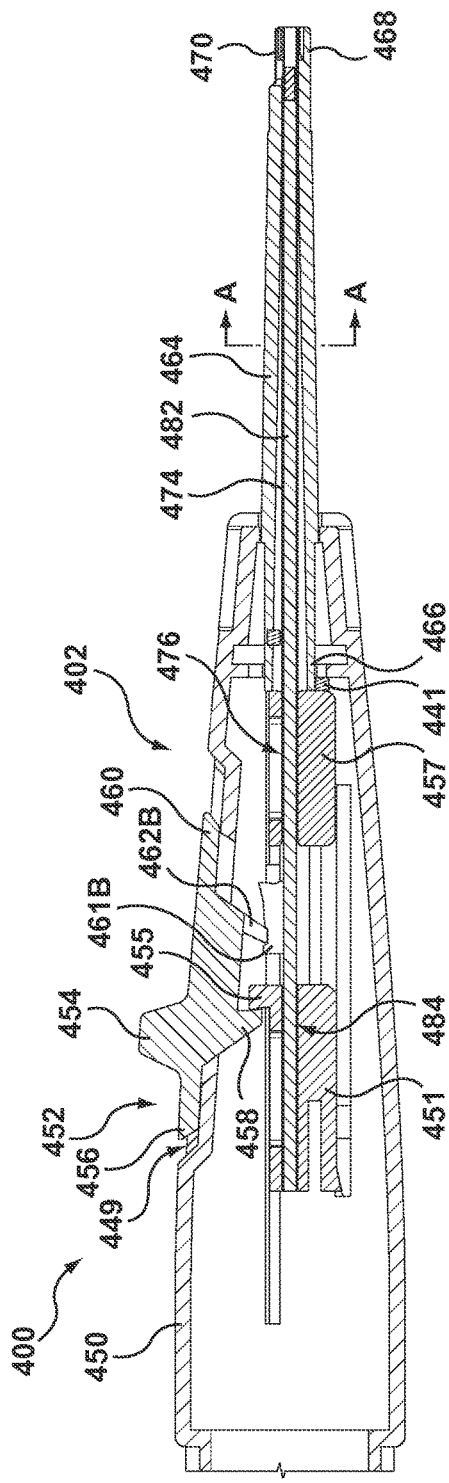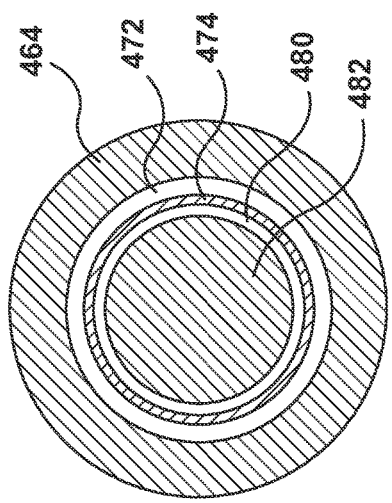
FIG. 6
FIG. 6A

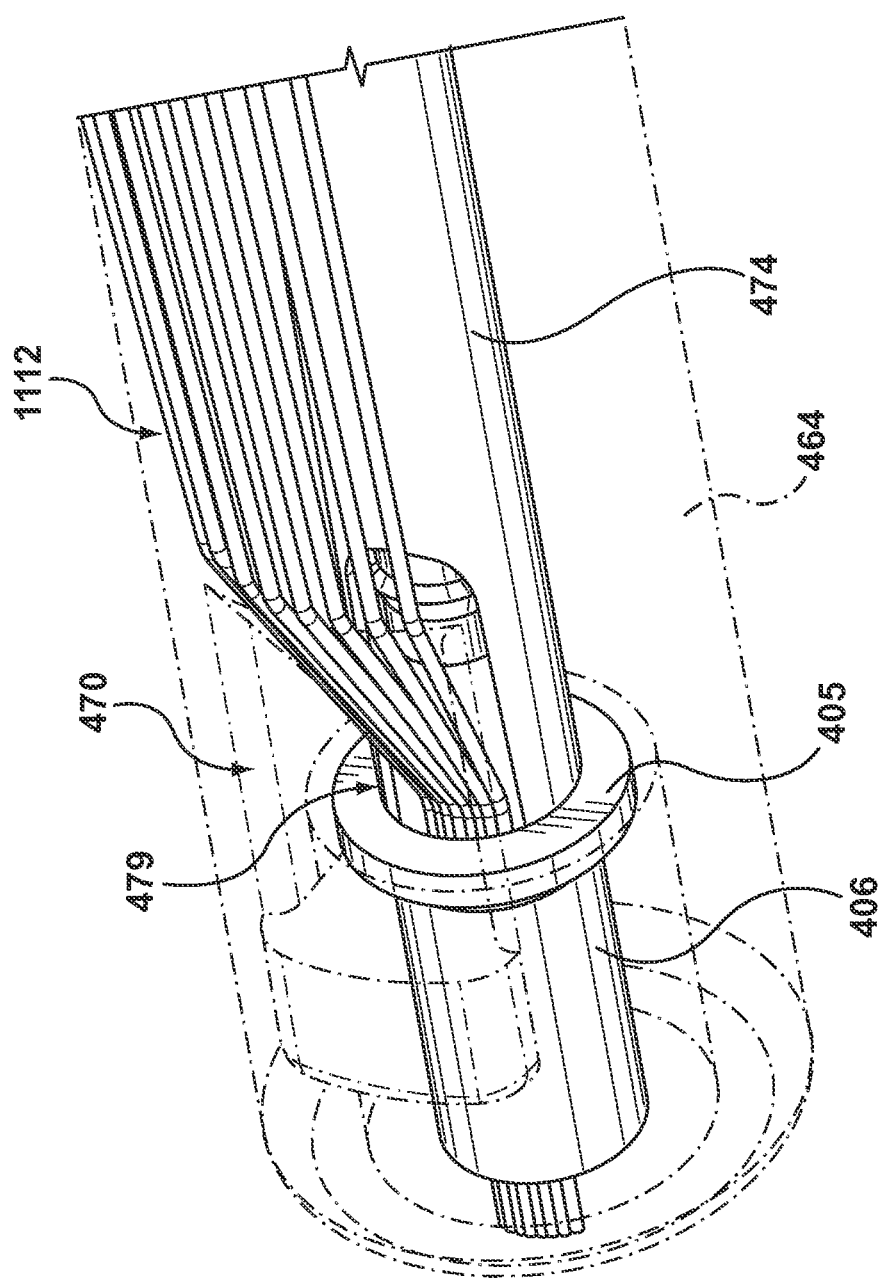

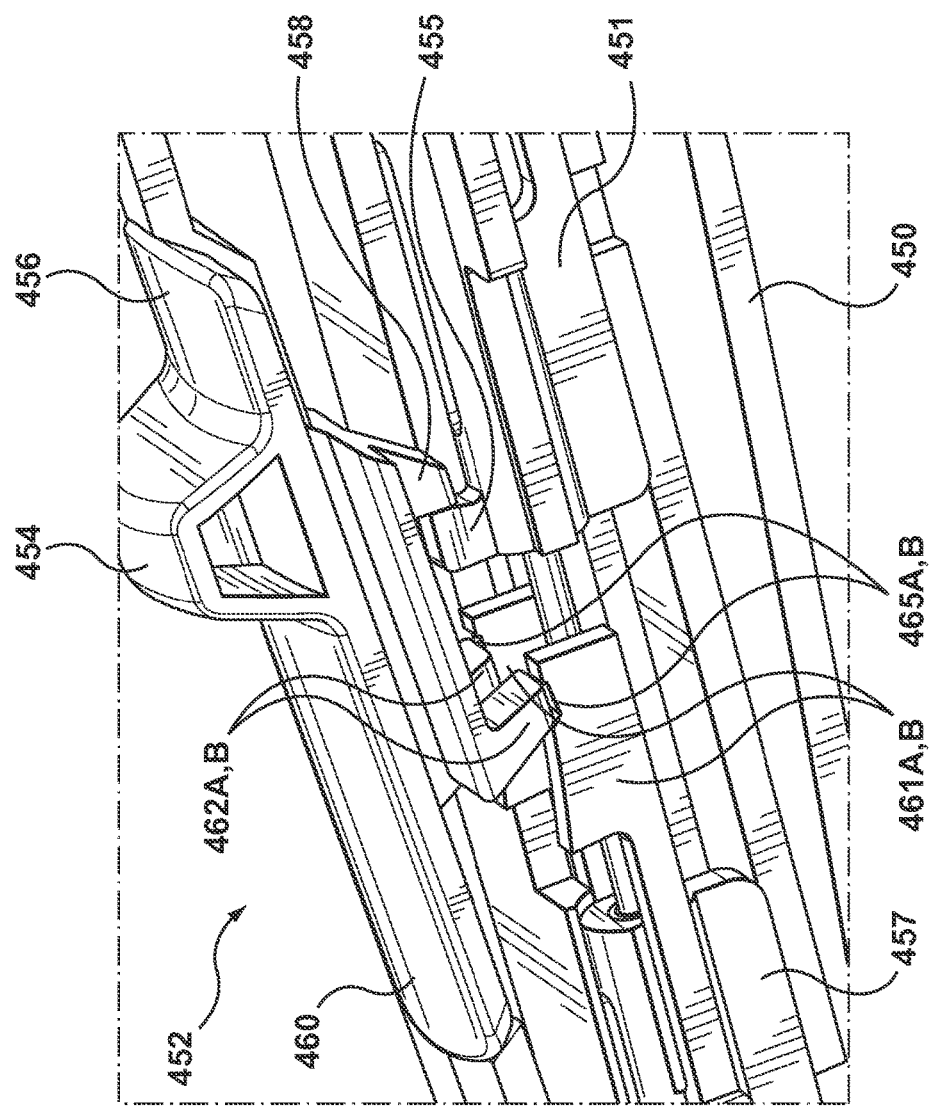

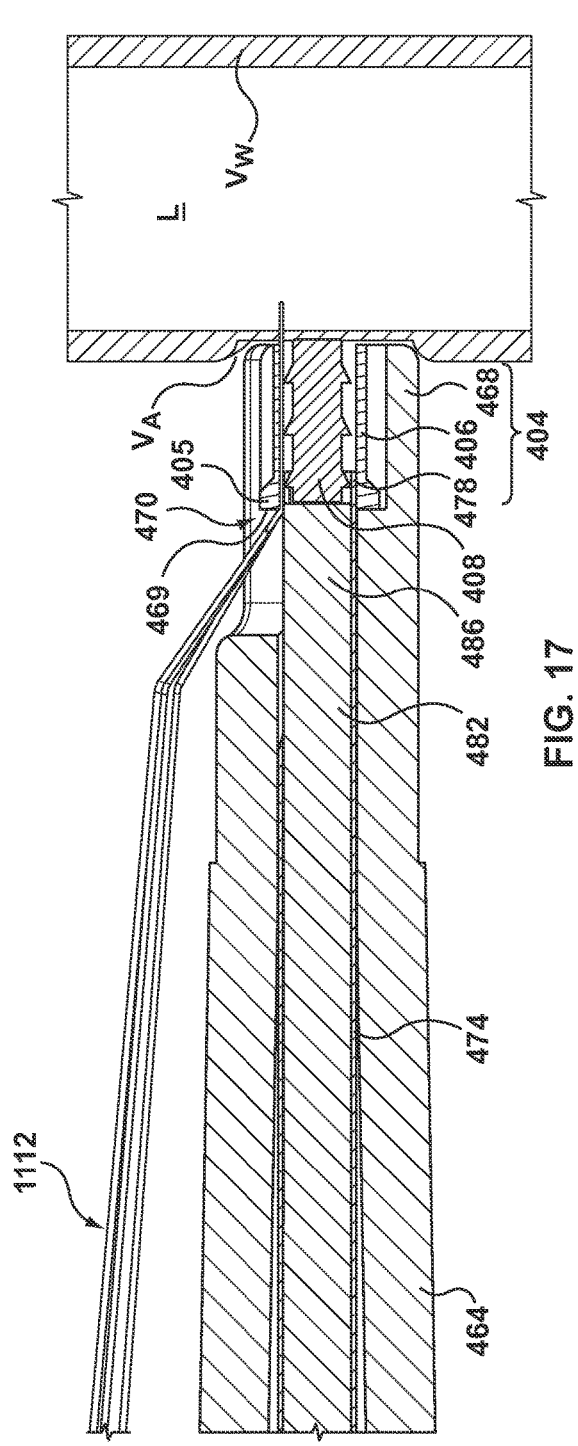
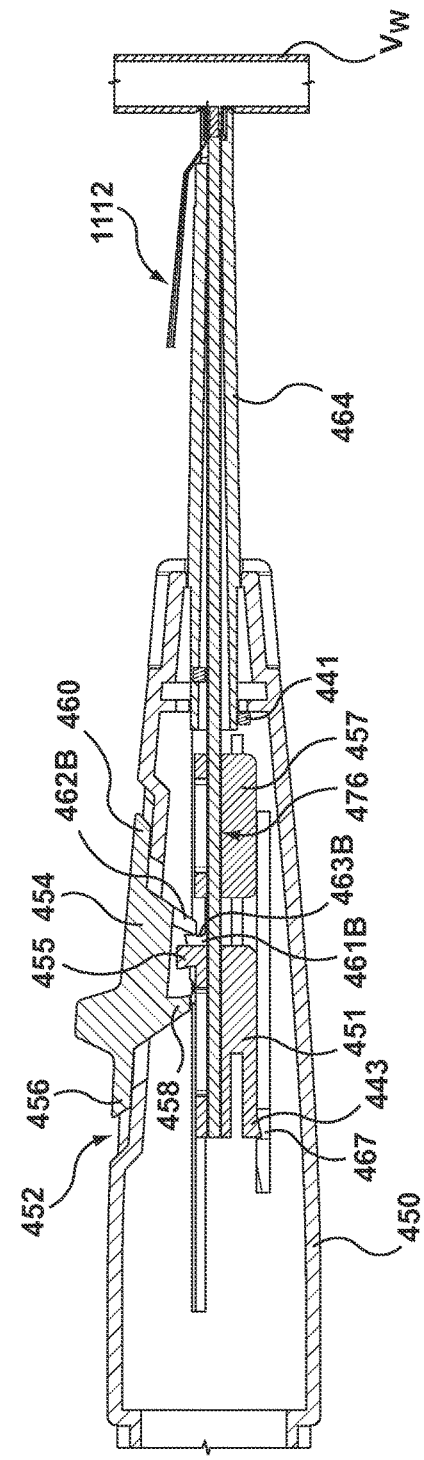

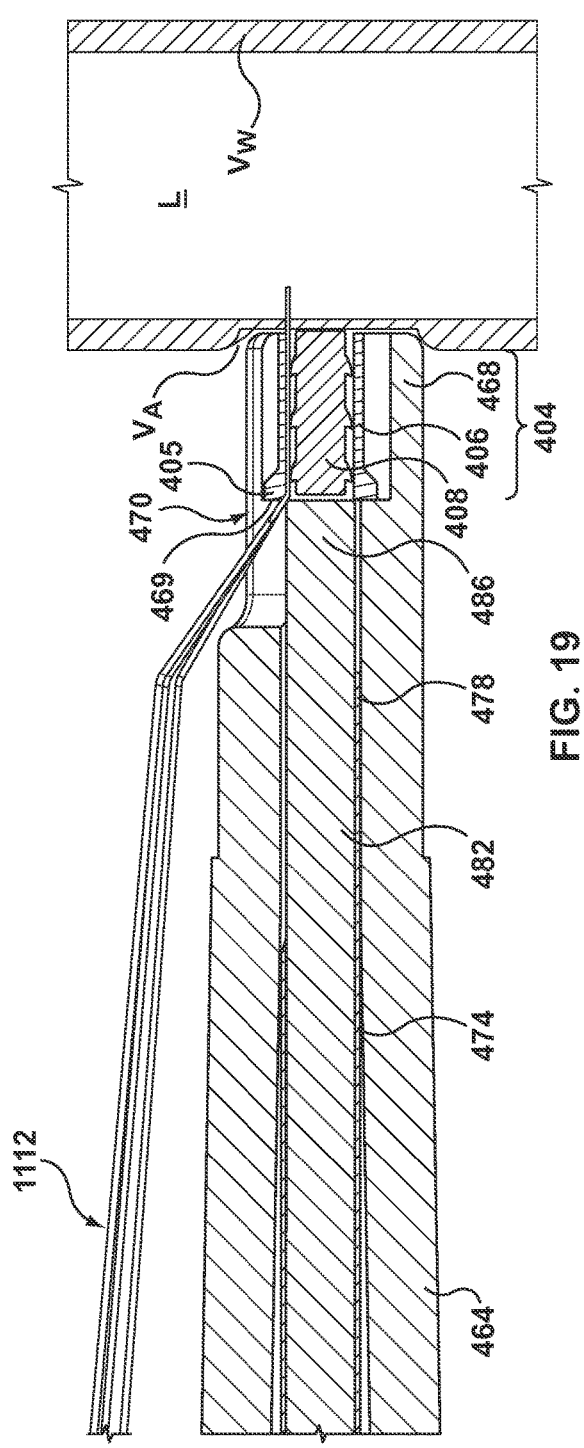
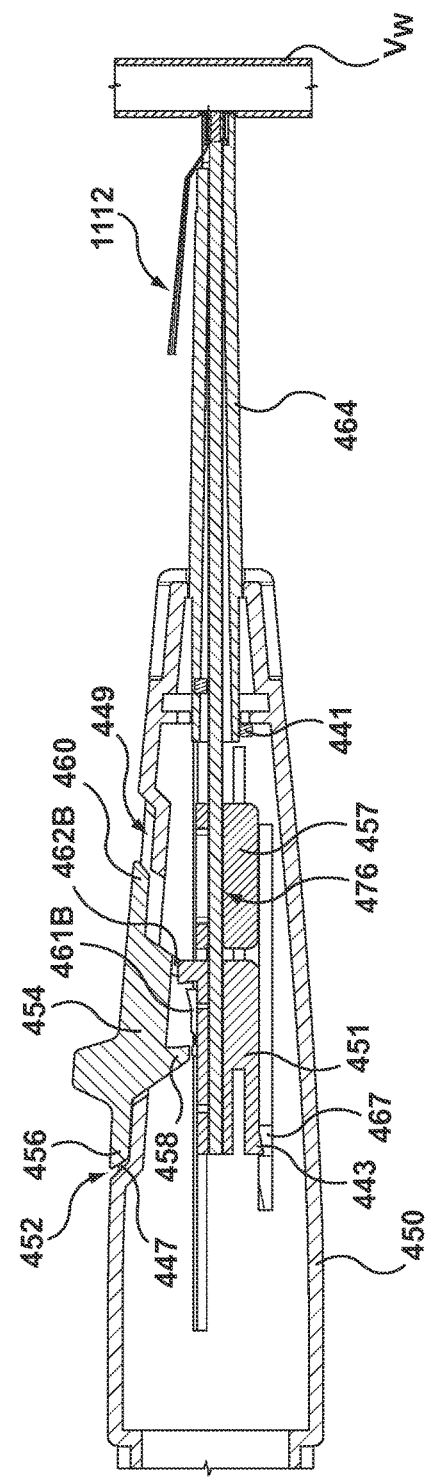
FIG. 19
FIG. 20

… (1 / 2)

METHOD AND APPARATUS FOR FORMING A SUTURE CONNECTOR IN SITU

FIELD OF THE INVENTION

Embodiments hereof relate to medical suturing devices. More particularly, embodiments hereof relate to devices and methods for securing suture portions extending from an opening in an arterial or other biological tissue wall that is not directly accessible to the physician.

BACKGROUND OF THE INVENTION

Various cardiovascular procedures, such as angioplasty, stent placement and atherectomy, require gaining access to the vasculature. With reference to FIGS. 1 and 2, access to the vasculature of a patient typically is through the femoral artery and is percutaneous, involving insertion of a needle (not shown), and in some cases a dilator (not shown), in the region of the groin to form a track 103 through subcutaneous tissue T and to puncture and create an arteriotomy $V_A$ in a vessel wall $V_W$ of the femoral artery. A guidewire GW is then advanced through the needle and into the femoral artery. The needle and dilator, if present, are then removed. An introducer sheath 101, which is typically a single lumen catheter with a hemostasis valve on its proximal end, or other interventional device is then advanced over the guidewire GW, along the track 103 and into the femoral artery in order to perform the selected procedure. Introducer sheath 101 provides access into the femoral artery, through the arteriotomy, for longer guidewires, catheters or other instrumentalities in order to perform the selected procedure. The hemostasis valve on the introducer sheath is used to prevent extraneous bleed back or to introduce medication into the patient's body.

After the procedure has been completed, the interventional devices are removed and the arteriotomy must be closed. The size of the puncture opening in the artery corresponds to the size of the catheter or percutaneous introducer sheath used, and such devices may typically range in diameter from 5 French for a diagnostic procedure to 6-20 French for a therapeutic procedure. A number of techniques are known to facilitate closure and healing of the arteriotomy. One technique includes application of pressure at the puncture site for a relatively extended length of time. More particularly, compression has traditionally been applied to the puncture site for at least 30-45 minutes for the wound to close naturally after removal of the catheter. Patients are required to remain lying down, essentially motionless and often with a heavy sandbag placed on their upper leg, for several hours to ensure that the bleeding has stopped. The recovery time from the medical procedure may be as little as half of an hour, but the recovery time from the wound can exceed twenty-four hours. Longer recovery times may result in increased expenses, increased patient discomfort, and greater risk of complications. Other approaches to arteriotomy closure include a compression clamp device, a thrombotic or collagen plug, biological adhesives adapted to seal the arteriotomy, and/or stapling devices.

In addition, medical suturing systems have been proposed to facilitate closure and healing of the arteriotomy and resolve some of the concerns associated with arteriotomy closure after vascular catheterization procedures. In addition, beyond suturing devices utilized for closing arteriotomies, surgeons frequently encounter the need to close internal incisions, wounds, or otherwise joining tissue portions with a suture in situ. For example, FIG. 3 illustrates an incision 310 in the patient's skin used to perform a percutaneous or minimally invasive treatment on the patient. After the patient has been treated, a suture 312 is introduced into the patient through an introducer sheath 301 for the purpose of drawing together tissue portions 316, 318 (shown in phantom in FIG. 3). Two end portions 320, 322 of suture 312 extend from the tissue portions 316, 318, respectively, which may, for example, be the result of an internal wound or an arteriotomy in a blood vessel or an organ. Suture 312 may be introduced into the patient and positioned through tissue portions 316, 318 by any suitable manner or device, including but not limited to those described in U.S. Pat. No. 6,117,144 to Nobles et al., U.S. Pat. No. 6,562,052 to Nobles et al., U.S. Pat. No. 7,803,167 to Nobles et al., U.S. application Ser. No. 13/802,551 to Argentine, filed Mar. 13, 2013, and U.S. application Ser. No. 13/802,563 to Argentine, filed Mar. 13, 2013, all of which are hereby incorporated by reference in their entirety. Suture 312 is shown in FIG. 3 extending from catheter sheath introducer 301, but may alternatively extend directly from incision 310 in the patient.

After passing suture 312 through the tissue portions, i.e., after the suture has been positioned adjacent to the internal wound or arteriotomy, the two end portions 320, 322 of suture 312 must be tied or otherwise coupled together to draw the tissue portions together and prevent them from separating. The two end portions 320, 322 may be manually tied by the surgeon. However, sutures can often be difficult to handle and/or access, thereby increasing the procedure time. Thus, in some instances, surgeons prefer to use a device that secures or couples the two end portions of a suture in situ. For example, U.S. Pat. Nos. 8,197,497 and 8,469,975 to Nobles et al., which are assigned to the same assignee as the present application and are herein incorporated by reference in their entirety, describes a knot placement device that positions a knot or connector that secures or couples the two end portions of a suture in situ. The knot includes a knot body and a plug, and the knot placement device pushes a plug distally into the knot body and traps at least two suture portions between the plug and the knot body. The knot, i.e., the knot body and the plug, having the suture portions trapped therein may then be ejected out of the knot placement device. When ejected out of the knot placement device, the knot may be inadvertently pushed through the opening or arteriotomy of the treatment site. In addition to possibly losing or reducing hemostasis, if inadvertently pushed through the arteriotomy, the knot may contact and damage the inner vessel wall opposite the incision/arteriotomy.

Embodiments hereof relate to improvements of a device that secures or couples two or more suture portions.

BRIEF SUMMARY OF THE INVENTION

Embodiments hereof relate a system for forming a suture connector in situ including a suture connector placement device and a suture connector. The suture connector placement device includes a handle having an actuating mechanism, an outer shaft, an intermediate shaft, and a push rod. The outer shaft defines a lumen from a proximal end to a distal end thereof. The proximal end of the outer shaft is coupled to the handle and the outer shaft includes a side opening adjacent to the distal end thereof. The intermediate shaft defines a lumen from a proximal end to a distal end thereof. The intermediate shaft is slidingly disposed within the lumen of the outer shaft with the proximal end of the intermediate shaft being coupled to the actuating mechanism of the handle. The push rod is slidingly disposed within the lumen of the intermediate shaft. The proximal end of the push rod is coupled to the actuating mechanism of the handle. The suture connector includes a sleeve and a plug. When the suture connector is in a loaded configuration within the suture connector placement device, the sleeve of the suture connector is disposed on an outer surface of the intermediate shaft within the lumen of the outer shaft adjacent to the distal end thereof and the plug of the suture connector is slidably disposed within the lumen of the intermediate shaft proximal of the sleeve.

Embodiments hereof also relate a system for forming a suture connector in situ including a suture connector placement device and a suture connector. The suture connector placement device includes a handle having an actuating mechanism, an outer shaft, an intermediate shaft, and a push rod. The outer shaft defines a lumen from a proximal end to a distal end thereof. The proximal end of the outer shaft is coupled to the handle and the outer shaft includes a side opening adjacent to the distal end thereof. The distal end of the outer shaft is configured to abut against an outer surface of a vessel wall. The intermediate shaft defines a lumen from a proximal end to a distal end thereof. The intermediate shaft is slidingly disposed within the lumen of the outer shaft with the proximal end of the intermediate shaft being coupled to the actuating mechanism of the handle. The actuating mechanism is configured to proximally retract the intermediate shaft. The push rod is slidingly disposed within the lumen of the intermediate shaft. The proximal end of the push rod is coupled to the actuating mechanism of the handle, and the actuating mechanism is configured to distally advance the push rod. The suture connector includes a sleeve formed of a resilient material and a plug. When the suture connector is in a loaded configuration within the suture connector placement device, the sleeve of the suture connector is disposed on an outer surface of the intermediate shaft within the lumen of the outer shaft adjacent to the distal end thereof and the plug of the suture connector is slidably disposed within the lumen of the intermediate shaft proximal of the sleeve. Distal advancement of the push rod moves the plug to longitudinally position the plug within the sleeve and proximal retraction of the intermediate shaft releases the sleeve onto the plug.

Embodiments hereof also relate to a method for securing two suture portions extending from an opening in body tissue. The two suture portions are positioned within a sleeve of a suture connector. The sleeve is disposed within a suture connector placement device including an outer shaft with a side opening proximal to its distal end, an intermediate shaft slidingly disposed through a lumen of the outer shaft, and a push rod slidingly disposed through a lumen of the intermediate shaft. The sleeve of the suture connector is disposed on an outer surface of the intermediate shaft within the lumen of the outer shaft adjacent to the distal end thereof and the plug of the suture connector being slidably disposed within the lumen of the intermediate shaft proximal of the sleeve. The outer shaft is advanced until the distal end of the outer shaft abuts against an outer surface of the vessel wall and surrounds the opening of the body tissue. The push rod is distally advanced relative to the intermediate shaft to slide the plug within the lumen of the intermediate shaft until the plug is longitudinally positioned within the sleeve thereon. The intermediate shaft is proximally retracted relative to the push rod to free the sleeve from contact with the outer surface of the intermediate sleeve such that the sleeve releases onto the plug, thereby securing the two suture portions between the sleeve and the plug.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 4 is a side view of a suture connector placement device for positioning a suture connector in situ according to an embodiment hereof.

FIG. 5 is a side view of a suture connector to be used with the suture connector placement device of FIG. 4, wherein the suture connector includes a plug and a sleeve.

FIG. 6 is a sectional view of a system of the suture connector of FIG. 5 positioned within a distal portion of the suture connector placement device of FIG. 4, wherein the suture connector is in a loaded or delivery configuration within the suture connector placement device.

FIG. 6A is a cross-sectional view of FIG. 6 taken along line A-A of FIG. 6.

FIGS. 11, 11A, 12, 12A, 13-15, 16, 16A, 17-19, 20 and 20A illustrate a method of using the suture connector placement device of FIG. 6 to secure suture portions extending from an arteriotomy in the vessel wall of a vessel.

DETAILED DESCRIPTION OF THE INVENTION

Figure 1:
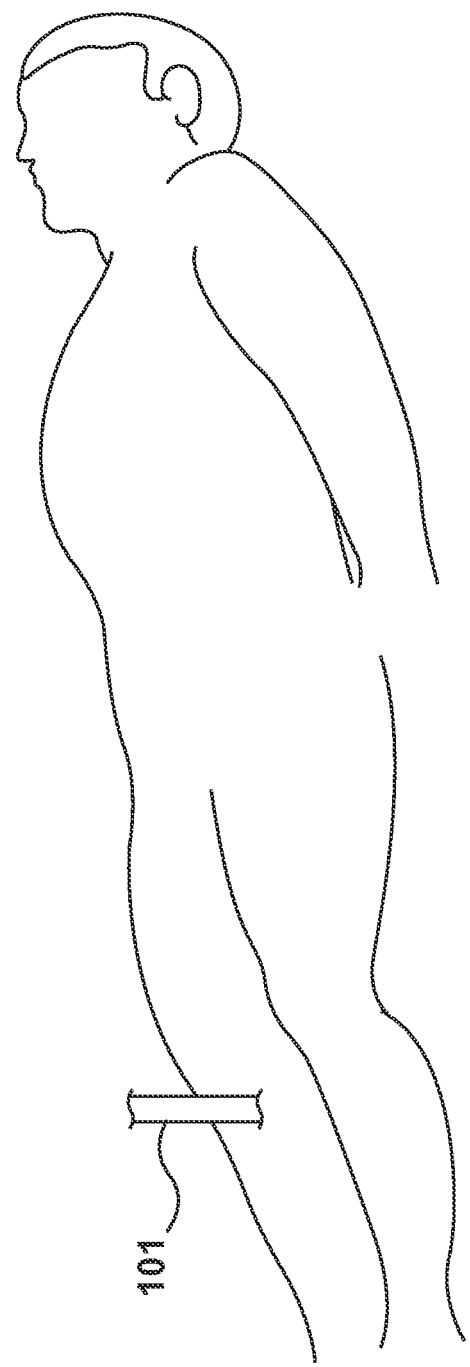
FIGS. 1 and 2 illustrate the introduction of an introducer sheath into the vasculature via the femoral artery, thereby forming an arteriotomy in a vessel wall of the femoral artery.
Figure 2:
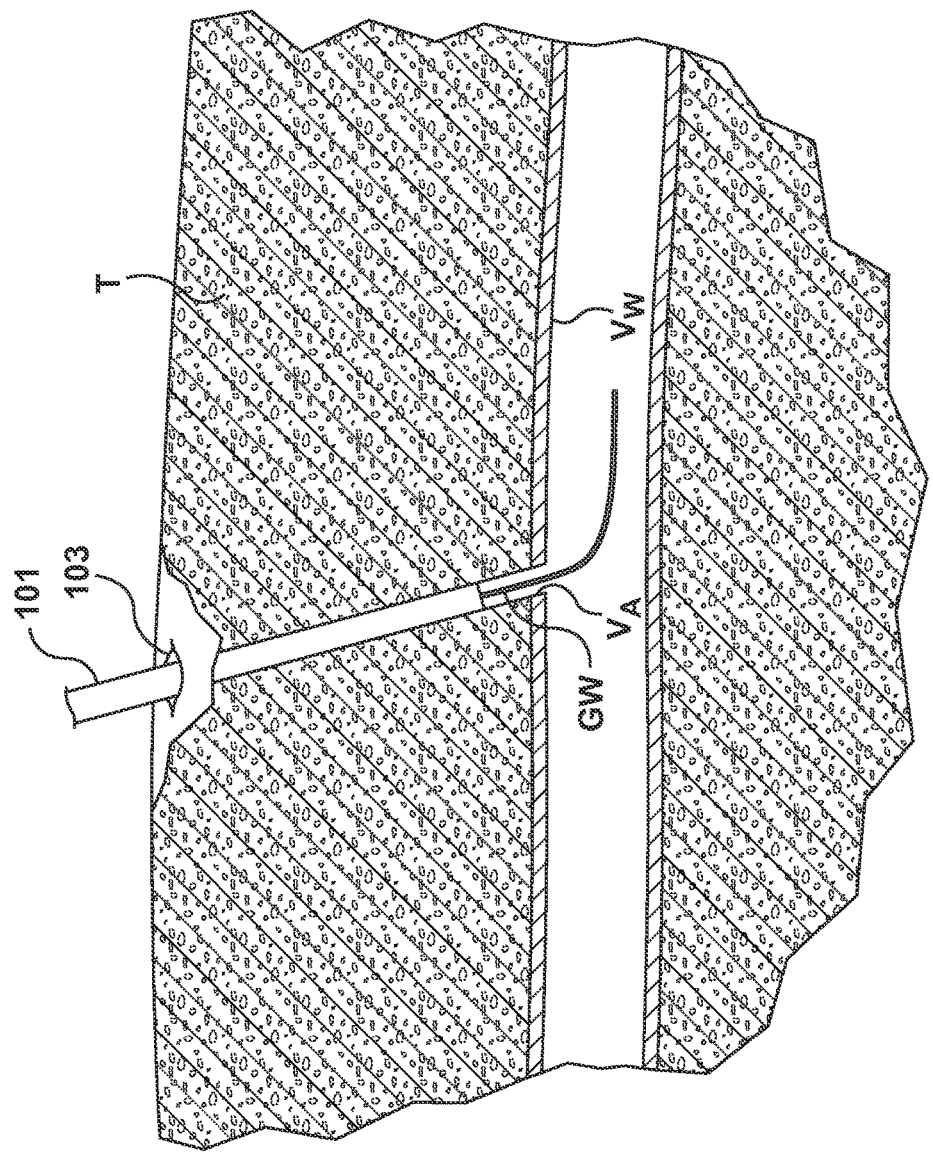
Figure 3:
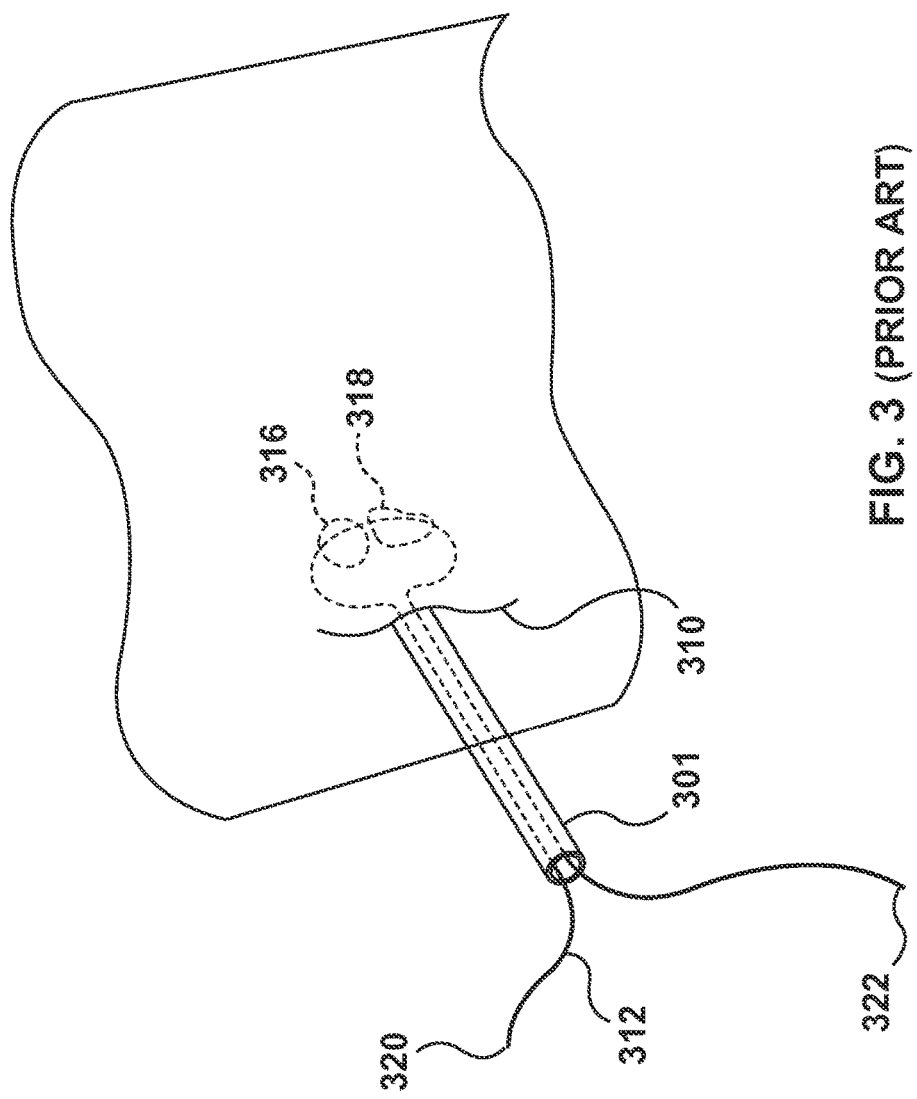
FIG. 3 is a perspective view of a wound site having a pair of suture ends extending therefrom.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Embodiments described below relate to a device for securing or coupling two suture portions extending from a treatment location of a patient, or otherwise stated for applying a connector to two suture portions extending from a treatment location of a patient. Suture portions may be portions of the same suture or may be portions of separate and different sutures. The treatment location may be any desired location, such as an arterial or venous blood vessel. Although the description of the invention is in the context of treatment of blood vessels, the invention may also be used in any other body passageways where it is deemed useful. For example, the device could be used to suture other tissue such as a patent ductus arteriosus, a patent foramen ovale, a heart defect, a puncture wound, and the like. There is no intention to be bound by any expressed or implied theory presented in the preceding technical field, background, brief summary or the following detailed description.

FIG. 4 illustrates a side view of a suture connector placement device 402 for positioning a knot or suture connector 404 in situ, while FIG. 5 is a side view of suture connector 404. Collectively, suture connector placement device 402 and suture connector 404 may be considered a system 400 for forming a suture connector in situ. Suture connector placement device 402 includes a handle 450 having an actuating mechanism 452 therein and an outer shaft 464 distally extending from handle 450. Suture connector 404 includes a cylindrical component or plug 408 and a tubular component or sleeve 406 which defines a lumen 407 there-through. Sleeve 406 includes a circumferential flange 405 radially extending from its outer surface. Flange 405 functions to interact with suture connector placement device 402 during operation thereof, as will be described in more detail herein. Plug 408 has an outer dimension and a length configured to be inserted into the lumen 407 of sleeve 406. Plug 408 may include radial protrusions 409 extending from its outer surface to ensure an interference or press fit between plug 408 and sleeve 406 when the plug and the sleeve are assembled or joined as will be described in more detail herein. Protrusions 409 may be rings, spirals, spikes, bumps, or other suitable structures. When loaded into suture connector placement device 402, as will be explained in more detail below, sleeve 406 and plug 408 are disposed within a distal end of the device such that plug 408 is positioned proximal of sleeve 406. Operation of suture connector placement device 402 to fully deploy and form suture connector 404 in situ may be considered a two-stage or two-step deployment process. In a first step or stage of the deployment operation that will be described in more detail herein, suture connector placement device 402 causes plug 408 to be distally advanced or pushed into sleeve 406, although sleeve 406 and plug 408 are not yet in contact with each other at this stage of deployment. Once the sleeve and plug are longitudinally aligned with each other, suture connector 404 is in a pre-deployed configuration. In a second step or stage of the deployment operation that will be described in more detail herein, suture connector placement device 402 causes sleeve 406 to be released onto plug 408, thereby securing or clamping suture portions (not shown in FIGS. 4-5) between the plug and the sleeve to thereby secure or hold the suture portions together relative to each other within the formed connector. The suture portions are secured or coupled together via the interference or press fit between plug 408 and sleeve 406. Once the sleeve is released onto the plug, suture connector 404 is formed and in a fully deployed configuration. Suture connector 404 may be used to secure suture portions that are positioned adjacent to an opening or arteriotomy of a blood vessel or other biological tissue following an interventional catheterization procedure, thereby closing or sealing the opening or arteriotomy to achieve hemostasis.

Correct positioning of suture connector 404 is essential for achieving closure of the opening or arteriotomy and hemostasis at the treatment site. In order to ensure that suture connector 404 is correctly positioned at a treatment site and hemostasis occurs, suture connector placement device 402 is designed such that outer shaft 464 abuts against tissue of the treatment site, with the distal end thereof disposed over or covering the opening or arteriotomy of the treatment site, and is designed such that suture connector 404 is not pushed or ejected out of the device after plug 408 is positioned within sleeve 406. Such a design ensures that suture connector 404 is correctly positioned against tissue of the treatment site and is not inadvertently pushed through the opening or arteriotomy of the treatment site. In addition, suture connector placement device 402 is designed to permit adjustment of suture portions after plug 408 is positioned within sleeve 406. Rather than locking or clamping suture portions in between the plug and sleeve as soon as the device has been fired or deployed, the two-stage deployment operation of system 400 permits a user to pull or tighten the suture portions if needed after plug 408 is positioned into sleeve 406, i.e., after suture connector 404 has been pre-deployed, in order to ensure that hemostasis is achieved at the treatment site. Additional advantages or improvements of suture connector placement device 402 and connector 400 are discussed herein with reference to the figures.

Figure 7:
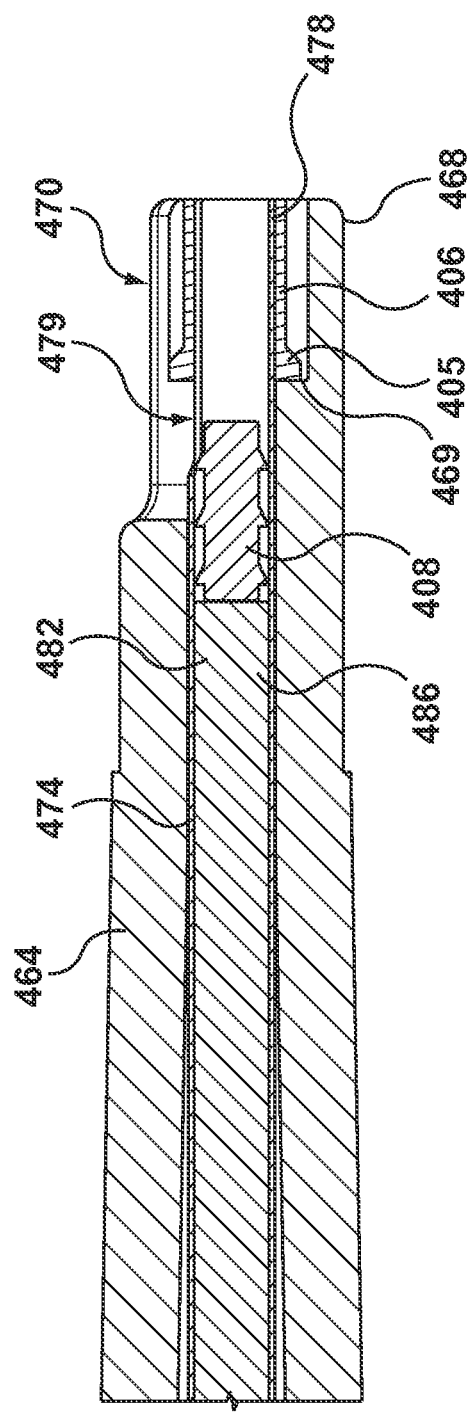
FIG. 7 is an enlarged view of a distal portion of FIG. 6.

The components of suture connector placement device 402 will now be described with reference to FIGS. 6, 6A, and 7. FIG. 6 is a sectional view of FIG. 4, FIG. 6A is a cross-sectional view taken along line A-A of FIG. 6, and FIG. 7 is an enlarged view of the distal end portion of FIG. 6. Suture connector placement device 402 includes outer shaft 464, an intermediate shaft 474, a push rod 482, and handle 450 having actuating mechanism 452 which includes a slider 454, a first coupler 451, and a second coupler 457. These components of suture connector placement device 402 may be made of any suitable material, including but not limited to metals, plastics, and a combination of metals and plastics. As best shown in FIG. 6A, intermediate shaft 474 is slidingly disposed through a lumen 472 of outer shaft 464, and push rod 482 is slidingly disposed through a lumen 480 of intermediate shaft 474. Outer shaft 464 is an elongate tubular component defining lumen 472 and has a proximal end 466 that extends into and is coupled to handle 450. A distal end 468 of outer shaft 464 is sized and configured to abut against an outer surface of a vessel wall or other body tissue. Distal end 468 is of sufficient size to be disposed over or cover the opening or arteriotomy of the treatment site. For example, the outer diameter of distal end 468 of outer shaft 464 may be between 15 and 20 French. Outer shaft 464 also includes a side opening or port 470 proximal to its distal end 468. Adjacent to distal end 468 of outer shaft 464, a distal portion of lumen 472 has a greater or larger diameter than the remaining proximal length thereof in order to create an abutment surface 469 along the inner surface of outer shaft 464. As will be explained in more detail herein, abutment surface 469 functions to hold sleeve 406 stationary when intermediate shaft 474 is retracted.

Intermediate shaft 474 is a tubular component defining lumen 480 and has a proximal end 476 that extends into and is attached to second coupler 457 of actuating mechanism 452, as will be explained in more detail herein. A distal end 478 of intermediate shaft 474 extends to distal end 468 of outer shaft 464. Intermediate shaft 474 also includes a side opening or port 479 proximal to its distal end 478. Since intermediate shaft 474 is retracted during operation of suture connector placement device 402 as will be described in more detail herein, in one embodiment, side port 479 extends to its distal end 478 to ensure alignment of side port 479 of intermediate shaft 474 and side port 470 of outer shaft 464 during device operation. As shown in the enlarged view of FIG. 7, sleeve 406 of suture connector 404 is disposed on an outer surface of intermediate shaft 474 within lumen 472 of outer shaft 464 adjacent to distal end 468 of the outer shaft when suture connector 404 is in a loaded configuration within suture connector placement device 402 as described in more detail with reference to FIGS. 11 and 12. Plug 408 of suture connector 404 is slidingly disposed within intermediate shaft 474, proximal to sleeve 406, when suture connector 404 is in a loaded configuration within suture connector placement device 402 as described in more detail with reference to FIGS. 11 and 12.

Push rod 482 is a solid cylindrical component and has a proximal end 484 that extends into and is attached to first coupler 451 of actuating mechanism 452, as will be explained in more detail herein. As shown in the enlarged view of FIG. 7, a distal end 486 of push rod 482 is positioned or disposed proximal to a proximal end of plug 408 when suture connector 404 is in a loaded configuration within suture connector placement device 402 as described in more detail with reference to FIGS. 11 and 12.

Figure 8:
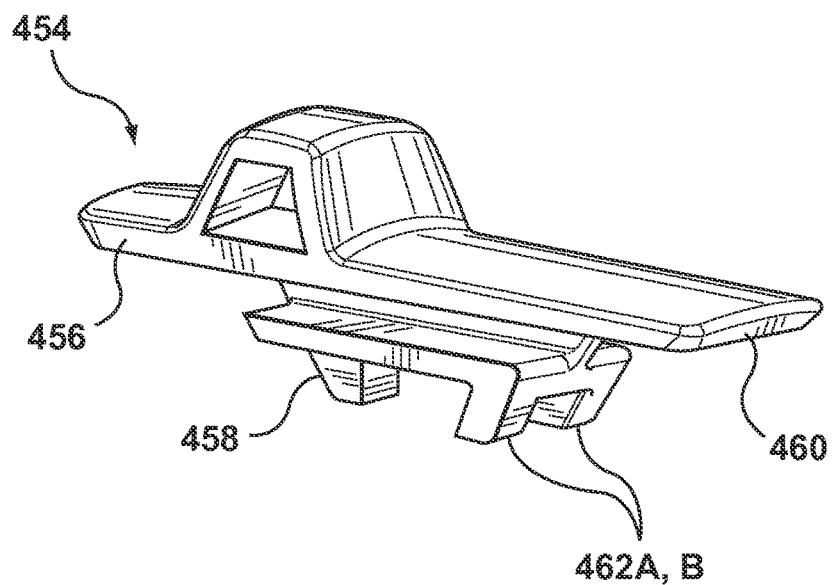
FIG. 8 is a perspective view of a slider of an actuating mechanism of the system of FIG. 6, wherein the slider is removed from a handle of the system for sake of illustration only.
Figure 9:
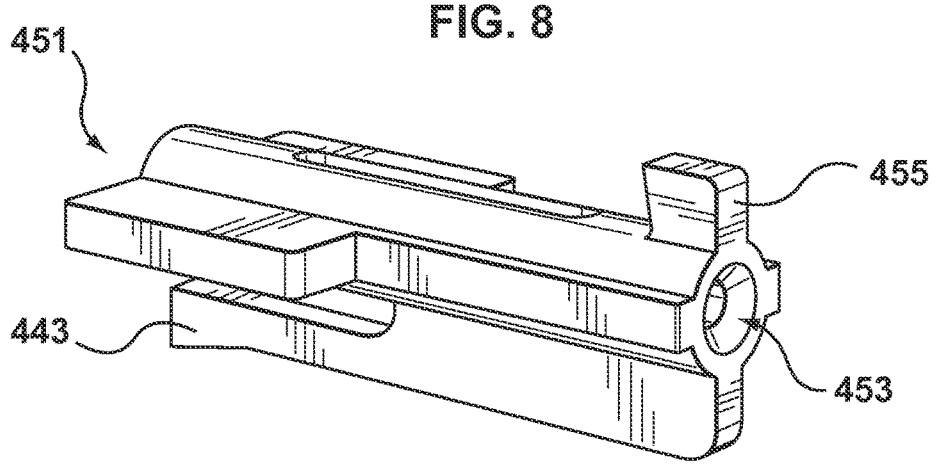
FIG. 9 is a perspective view of a first coupler of an actuating mechanism of the system of FIG. 6, wherein the first coupler is removed from a handle of the system for sake of illustration only.

Actuating mechanism 452 includes slider 454, first coupler 451 that couples proximal end 484 of push rod 482 to slider 454, and second coupler 457 that couples proximal end 476 of intermediate shaft 474 to slider 454. Actuating mechanism 452 is configured to distally advance push rod 482 via interaction between slider 454 and first coupler 451, and is also configured to proximally retract intermediate shaft 474 via interaction between slider 454 and second coupler 457. Advantageously, from a user perspective, operation of actuating mechanism 452 requires interaction with only slider 454, with distal advancement of slider 454 being employed in the first step or stage of deployment to push plug 408 into sleeve 406 and proximal retraction of slider 454 being employed in the second step or stage of deployment to retract intermediate shaft 474 and thereby release sleeve 406 onto plug 408. More particularly, slider 454 is housed within a recess 449 of the handle such that a top surface thereof is accessible to the user and a bottom or underside surface interacts with the remaining components of actuating mechanism 452. With additional reference to FIG. 8, slider 454 includes a proximal end 456 having a first knob or boss 458 on an underside surface thereof and a distal end 460 having a pair of spaced-apart knobs or bosses 462A, 462B on the underside surface thereof. With additional reference to FIG. 9, first coupler 451 includes a lumen 453 through at least a distal portion thereof for receiving proximal end 484 of push rod 482. First coupler 451 also includes a knob or boss 455 at its distal end that extends in an upward direction towards slider 454 for interaction or engagement with first knob 458 of slider 454, and a dovetail 443 at its proximal end that extends in a downwards direction away from slider 454 for locking or securing first coupler 451 and push rod 482 coupled thereto in an extended configuration as will be described in more detail herein. With additional reference to FIG. 10, second coupler 457 includes a lumen 459 there-through for receiving a proximal end 476 of intermediate shaft 474, as well as push rod 482 which is slidably disposed through intermediate shaft 474 and extends proximally to first coupler 451. A proximal portion of second coupler 457 also includes two spaced-apart rails 461A, 461B on opposing sides thereof for interaction or engagement with the pair of spaced-apart knobs or bosses 462A, 462B of slider 454. The proximal ends of rails 461A, 461B include grooves or notches 465A, 465B formed thereon for temporarily housing distal knobs 462A, 462B of slider 454 as will be described in more detail herein.

Figure 11:
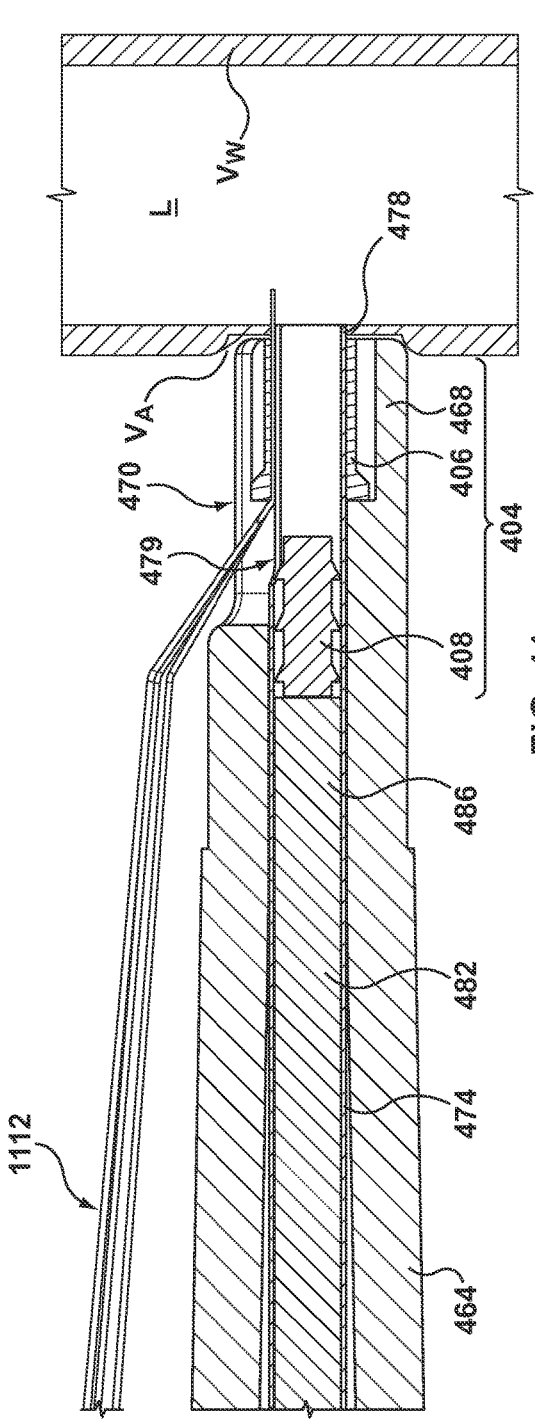
Figure 12:
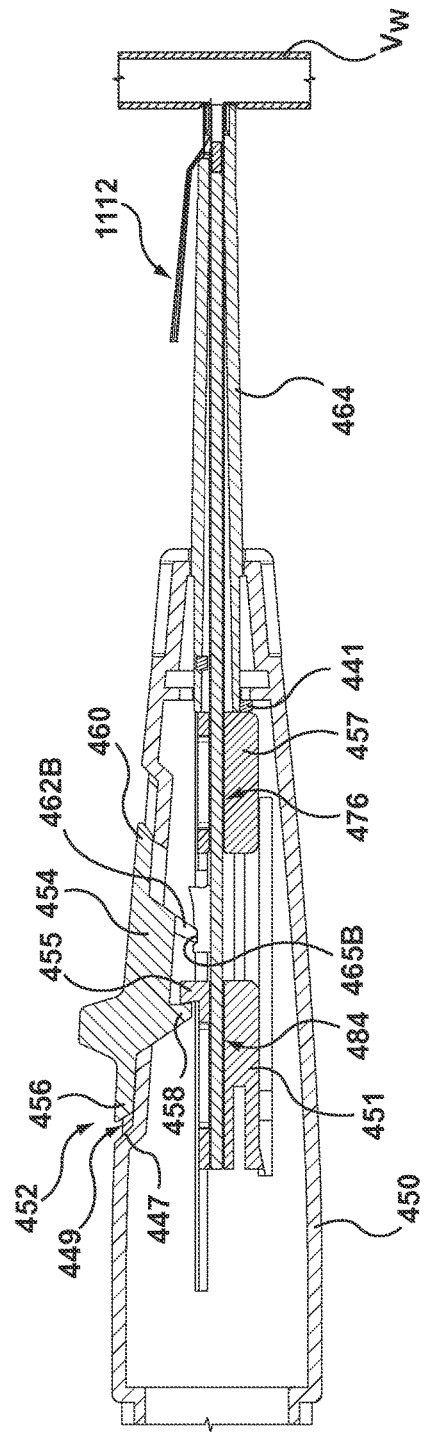

Since suture connector placement device 402 is utilized to clamp or secure portions of one or more sutures within suture connector 404, the suture portions having been previously positioned around the border or edge of an arteriotomy of a vessel, the components of the suture connector placement device will be further described while simultaneously describing a method of using the suture connector placement device to secure two suture portions extending from an opening in body tissue with reference to FIGS. 11-20. Referring to FIGS. 11, 12, and 12A, side sectional views of suture connector placement device 402 are shown with a distal end of the suture connector placement device abutting against tissue having an arteriotomy $V_A$ in the vessel wall $V_W$ of a vessel. FIG. 11 is an enlarged view of only the distal end of the suture connector placement device while FIG. 12 illustrates handle 450 of the suture connector placement device as well. FIG. 11A is a perspective view of a distal end of the suture connector placement device and FIG. 12A is a perspective view of a portion of handle 450.

In FIGS. 11, 11A, 12, and 12A, suture connector 404 is in a loaded or delivery configuration within suture connector placement device 402. More particularly, when suture connector 404 is in the loaded configuration, sleeve 406 of suture connector 404 is radially disposed between outer shaft 464 and intermediate shaft 474 adjacent to distal end 468 of outer shaft 464. Stated another way, sleeve 406 of suture connector 404 is disposed on an outer surface of intermediate shaft 474 within lumen 472 of outer shaft 464 adjacent to distal end 468 of the outer shaft. Flange 405 of sleeve 406 abuts against or is adjacent to abutment surface 469 of outer shaft 464. Plug 408 of suture connector 404 is positioned within lumen 480 of intermediate shaft 474 proximal of the proximal end of sleeve 406. In addition, distal end 486 of push rod 482 is positioned proximal to a proximal end of plug 408. Distal end 478 of intermediate shaft 474 is positioned flush with the distal end of sleeve 406 as well as flush with distal end 468 of outer shaft 464. Side port 479 of intermediate shaft 474 is circumferentially aligned with side port 470 of outer shaft 464. Proximal end 456 of slider 454 abuts against a proximal surface 447 of recess 449 within handle 450, with knob 458 of slider 454 abutting against knob 455 of first coupler 451. Second coupler 457 is positioned within a distal portion of handle 450 such that the distal end of second coupler 457 abuts against an interior surface or stopper 441 formed within the distal portion of handle 450. As best shown in the perspective view of FIG. 12A, distal knobs 462A, 462B of slider 454 are positioned or housed within grooves or notches 465A, 465B formed on the proximal ends of rails 461A, 461B of second coupler 457.

Suture portions 1112 are shown positioned within the distal portion of suture connector placement device 402 in FIGS. 11-12. Suture portions 1112 enter into a distal end of the suture connector placement device, extend through lumen 407 of sleeve 406 of suture connector 404, and exit suture connector placement device 402 via aligned side ports 470, 479 of outer shaft 464, intermediate shaft 474, respectively. Suture portions 1112 are portions of one or more sutures that were previously positioned around the border or edge of arteriotomy $V_A$ in the vessel wall $V_W$ of a vessel. Exemplary suture materials include but are not limited to a monofilament or plastic suture material, such as polypropylene. In the loaded configuration of suture connector 404 of FIGS. 11-12, and as best shown in the perspective view of FIG. 11A, suture portions 1112 are positioned or extend into and through sleeve 406 via aligned side ports 470, 479 of outer shaft 464, intermediate shaft 474, respectively. In order to position or load the suture portions into the suture connector placement device, suture connector placement device 402 may include a preloaded threader (not shown) as described in U.S. Pat. Nos. 8,197,497 and 8,469,975 to Nobles et al., both of which were previously incorporated herein by reference. The threader includes a tab and a looped wire passing through side port 470 of outer shaft 464 and between sleeve 406 and intermediate shaft 474. Suture portions 1112 are passed through the looped end of the wire, and the tab is pulled proximally to dispose suture portions 1112 in the suture connector placement device through sleeve 406.

Suture portions 1112 may be held in tension, by hand or otherwise, while suture connector placement device 402 is advanced until distal end 468 contacts and abuts against an outer surface of the vessel wall around the border or edge of arteriotomy $V_A$. As shown in FIG. 11, distal end 468 of outer shaft 464 is sized to abut against the outer surface of the vessel wall $V_W$ and not protrude or extend through the arteriotomy $V_A$ and into the lumen L of the vessel. When the user is advancing suture connector placement device 402 to the arteriotomy $V_A$, a resistance to further advancement is felt when distal end 468 contacts the vessel wall, thereby notifying the user that the suture connector placement device is in place adjacent to the arteriotomy $V_A$ as desired.

Figure 13:
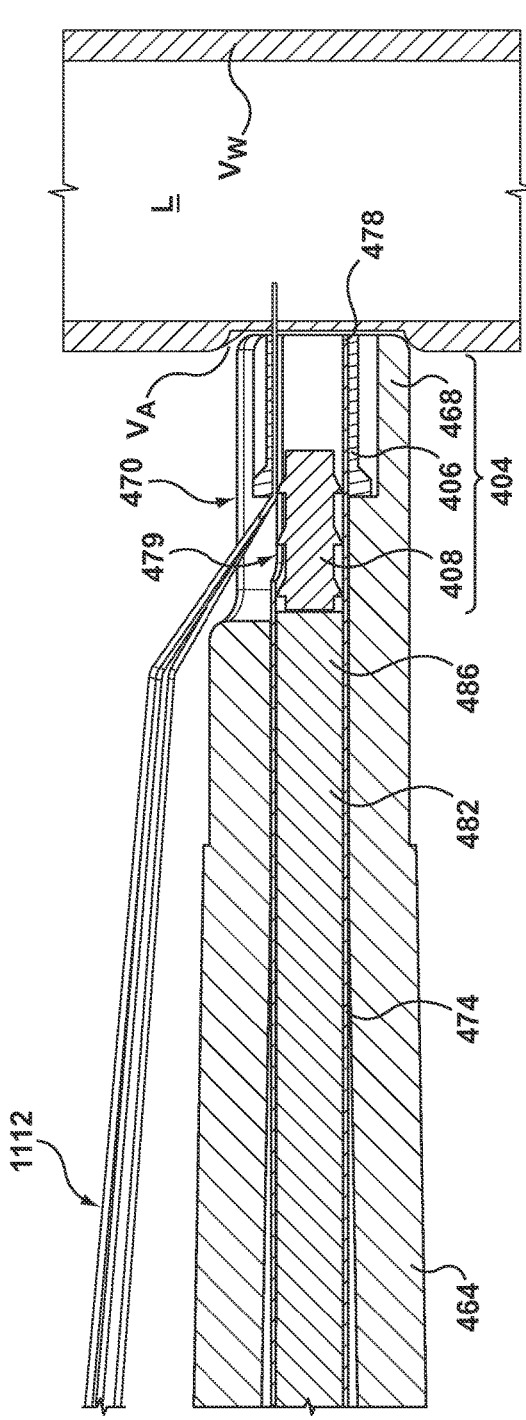
Figure 14:
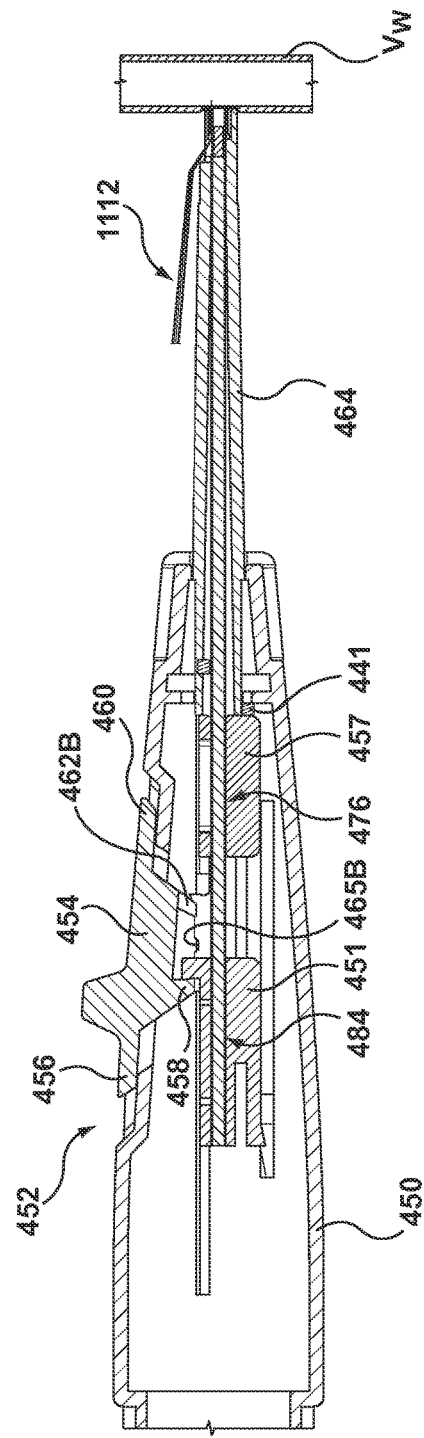

When it is desired to begin deployment of suture connector 404, slider 454 is distally advanced in order to distally advance plug 408 towards sleeve 406 as shown in FIGS. 13 and 14. FIG. 13 is an enlarged view of only the distal end of the suture connector placement device while FIG. 14 illustrates handle 450 of the suture connector placement device as well. More particularly, when slider 454 of actuating mechanism 452 is distally advanced or pushed forward, knob 458 of slider 454 pushes or distally advances knob 455 of first coupler 451, thereby also distally advancing coupler 451 and push rod 482 attached thereto. Distal end 486 of push rod 482 contacts and distally advances plug 408 through intermediate shaft 474. Thus, distal advancement of slider 454 also distally advances push rod 482 and plug 408 in unison. During advancement of push rod 482, intermediate shaft 474 remains stationary with distal end 478 thereof positioned flush with distal end of sleeve 406 as well as flush with distal end 468 of outer shaft 464. Further, during distal advancement of push rod 482, distal knobs 462A, 462B of slider 454 exit or are removed from grooves or notches 465A, 465B formed on the proximal ends of rails 461A, 461B of second coupler 457, and distal knobs 462A, 462B ride along or over rails 461A, 461B of second coupler 457. More particularly, since the distal end of second coupler 457 abuts against stopper 441 formed within the distal portion of handle 450, second coupler 457 and intermediate shaft 474 coupled thereto are fixed or locked and cannot be inadvertently distally advanced during distal advancement of first coupler 451 and push rod 482. With second coupler 457 fixed, rails 461A, 461B are leaf springs and bend or flex in a downward direction away from slider 454 when distal knobs 462A, 462B of slider 454 are distally advanced there-over. In addition, sleeve 406 of suture connector 404 remains radially disposed between outer shaft 464 and intermediate shaft 474 adjacent to distal end 468 of outer shaft 464 during advancement of push rod 482. Suture portions 1112 may be held in tension, by hand or otherwise, during distal advancement of push rod 482 and plug 408.

Figure 15:
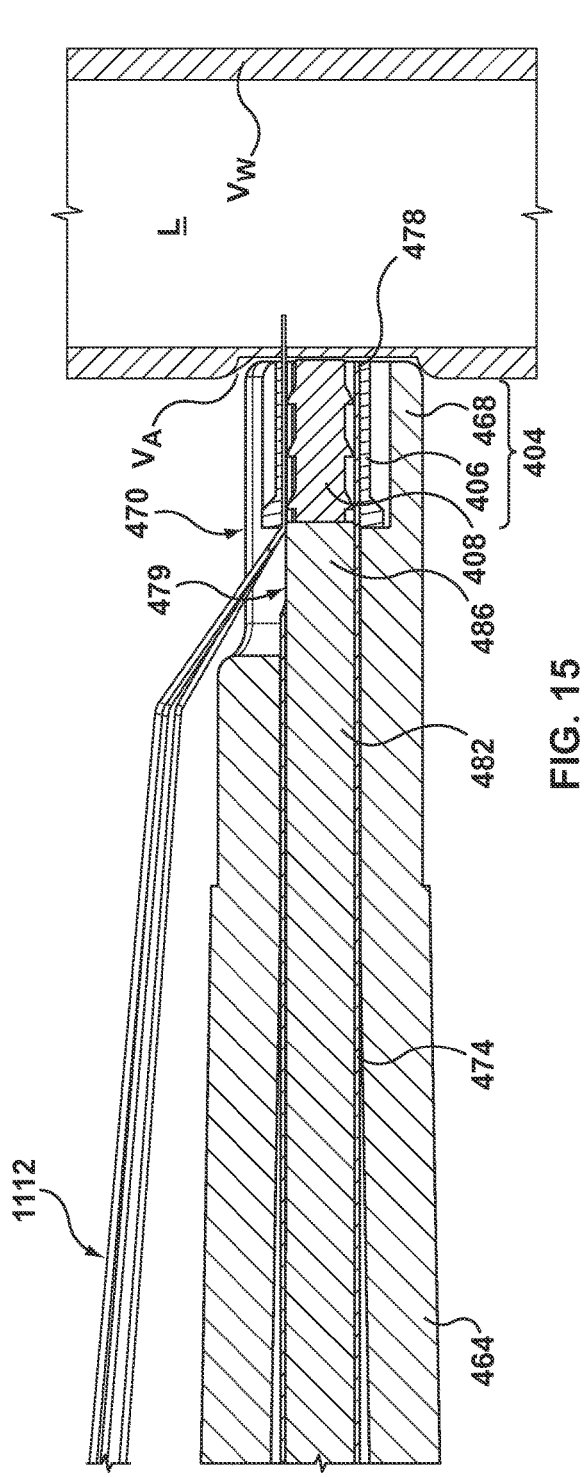
Figure 16:
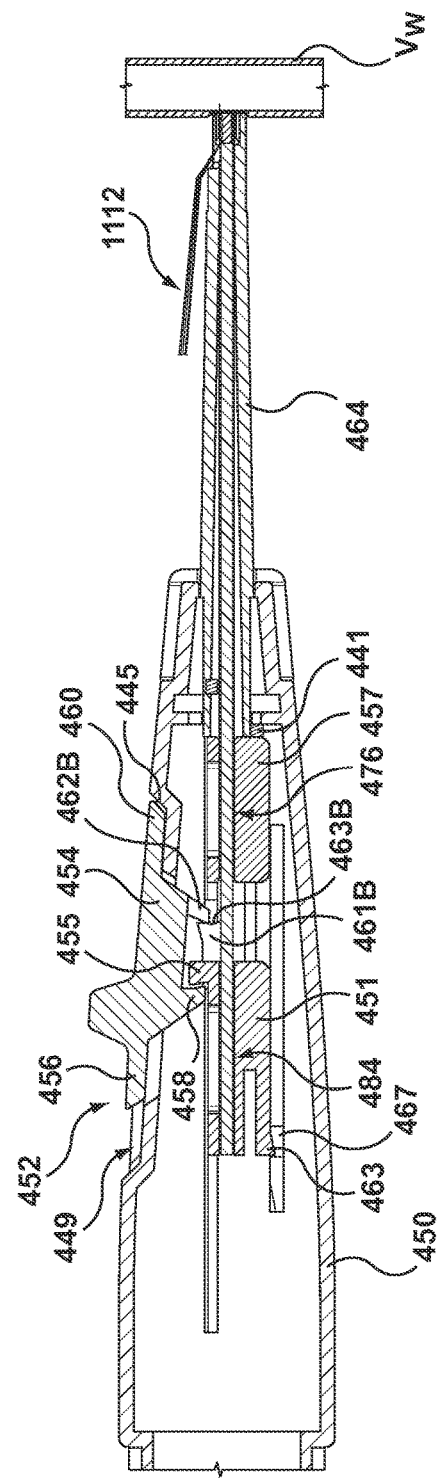
Figure 16A:
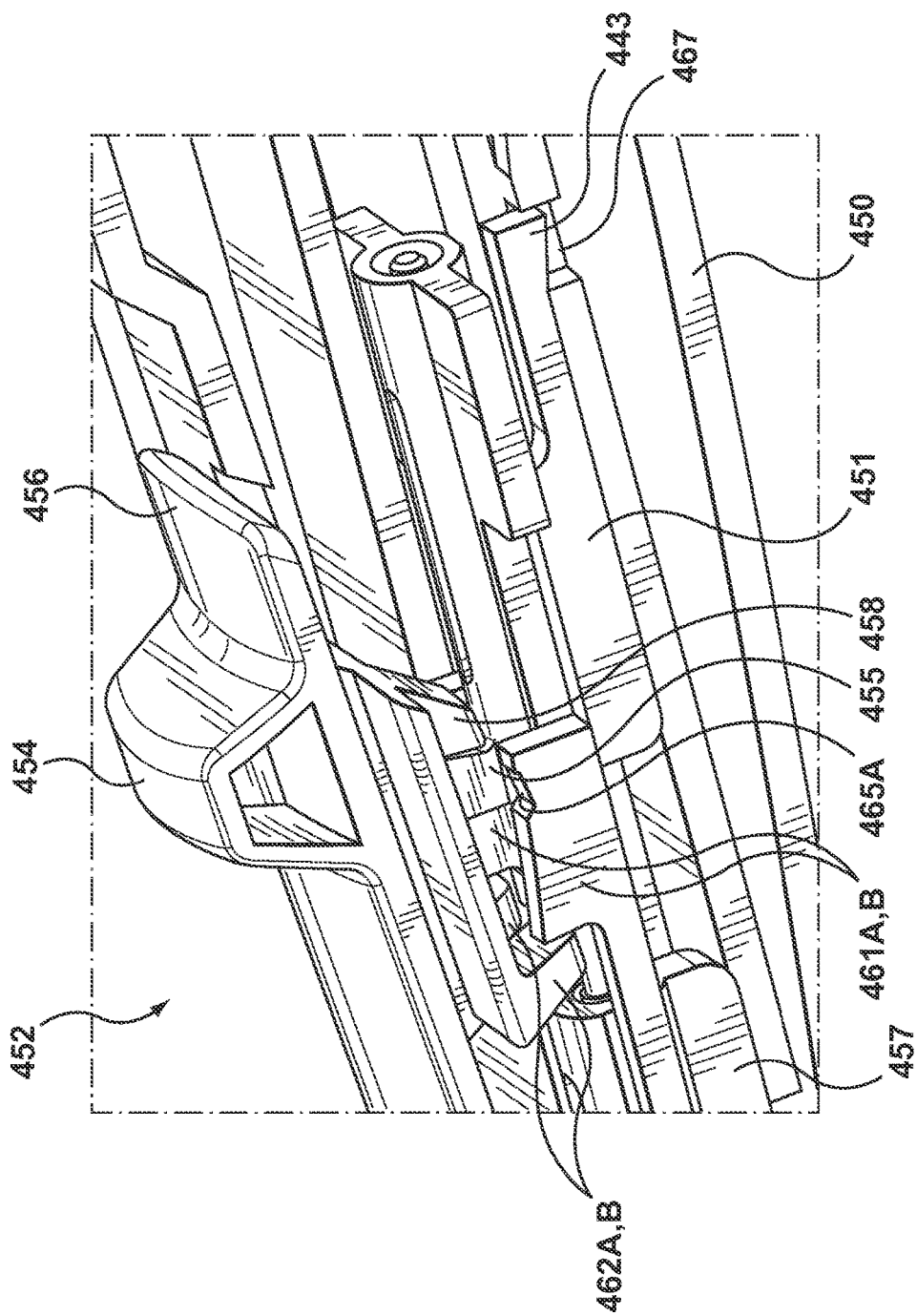

Slider 454 is distally advanced to the position shown in FIGS. 15 and 16, in which distal end 460 thereof abuts against a distal surface 445 of recess 449 within handle 450 and plug 408 is positioned within sleeve 406. FIG. 15 is an enlarged view of only the distal end of the suture connector placement device while FIG. 16 illustrates handle 450 of the suture connector placement device as well. FIG. 16A is a perspective view of a portion of handle 450. Although plug 408 is positioned within sleeve 406, plug 408 and sleeve 406 are not yet in contact with each other because intermediate shaft 474 is radially positioned there-between. At this point in the method of use, slider 454 and push rod 482 are each in an extended position and suture connector 404 may be considered to be in a pre-deployed configuration since plug 408 of suture connector 404 has been extended or relocated into sleeve 406 but is not yet in contact with sleeve 406. As best shown in FIG. 16A, when slider 454 and push rod 482 are in the extended configuration, dovetail 443 at the proximal end of first coupler 451 extends into or is housed within a recess or notch 467 formed within handle 450 for locking or securing first coupler 451 and push rod 482 coupled thereto in the extended configuration. With slider 454 in the extended position, distal knobs 462A, 462B of slider 454 pass over or are now located distal to rails 461A, 461B of second coupler 457. After distal knobs 462A, 462B of slider 454 are no longer causing rails 461A, 461B to bend or flex downward due to their leaf spring characteristics, rails 461A, 461B spring upward and assume their nominal positions, with distal knobs 462A, 462B engaging or abutting against distal surfaces 463A, 463B of rails 461A, 461B. Advantageously, suture portions 1112 may still be adjusted or tightened at this stage of deployment. Thus, if distal advancement of plug 408 causes loosening or movement of suture portions 1112, tension or other adjustments may be applied to suture portions 1112 during or after the step of positioning of plug 408 within sleeve 406.

Figure 10:
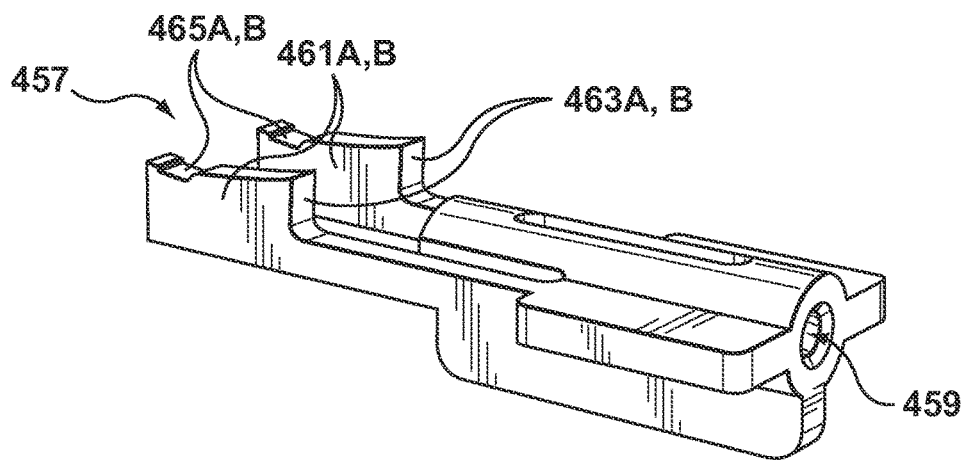
FIG. 10 is a perspective view of a second coupler of an actuating mechanism of the system of FIG. 6, wherein the second coupler is removed from a handle of the system for sake of illustration only.

Once suture portions 1112 have been adjusted or tightened as desired, intermediate shaft 474 is proximally retracted in order to release sleeve 406 onto plug 408. More particularly, when it is desired to complete deployment of suture connector 404, slider 454 is proximally retracted in order to proximally retract intermediate shaft 474 away from sleeve 406 as shown in FIGS. 17 and 18. FIG. 17 is an enlarged view of only the distal end of the suture connector placement device while FIG. 18 illustrates handle 450 of the suture connector placement device as well. More particularly, when slider 454 of actuating mechanism 452 is proximally retracted or pulled backwards, the pair of knobs 462A, 462B of slider 454 engages or abuts against distal surfaces 463A, 463B of rails 461A, 461B of second coupler 457. Although FIG. 15 is a sectional view and only knob 462B and rail 461B are shown, knob 462A and rail 461A are mirror images of knob 462B and rail 461B, respectively, as shown in FIG. 10, and as such, interactions there-between are the same. Slider 454 thus pushes or proximally retracts rails 461A, 461B of second coupler 457, thereby also proximally retracting second coupler 457 and intermediate shaft 474 attached thereto. During retraction of intermediate shaft 474 knob 458 of slider 454 is no longer in contact with knob 455 of first coupler 451 and passes or slides within a space between rails 461A, 461B of second coupler 457, such that push rod 482 remains stationary in the extended position during retraction of intermediate shaft 474. In addition, dovetail 443 at the proximal end of first coupler 451 being locked or secured within recess or notch 467 of handle 450 ensures that push rod 482 (which is attached to first coupler 451) is not inadvertently retracted with intermediate shaft 474. With push rod 482 locked in the extended position, plug 408 remains securely within sleeve 406 during retraction of intermediate shaft 474. In addition, during retraction of intermediate shaft 474, flange 405 formed on sleeve 406 engages or abuts against abutment surface 469 formed within outer shaft 464 to ensure that sleeve 406 is not inadvertently refracted with intermediate shaft 474. Thus, the interaction between abutment surface 469 and flange 405 of sleeve 406 ensures that sleeve 406 is held stationary when intermediate shaft 474 is retracted.

Figure 20A:
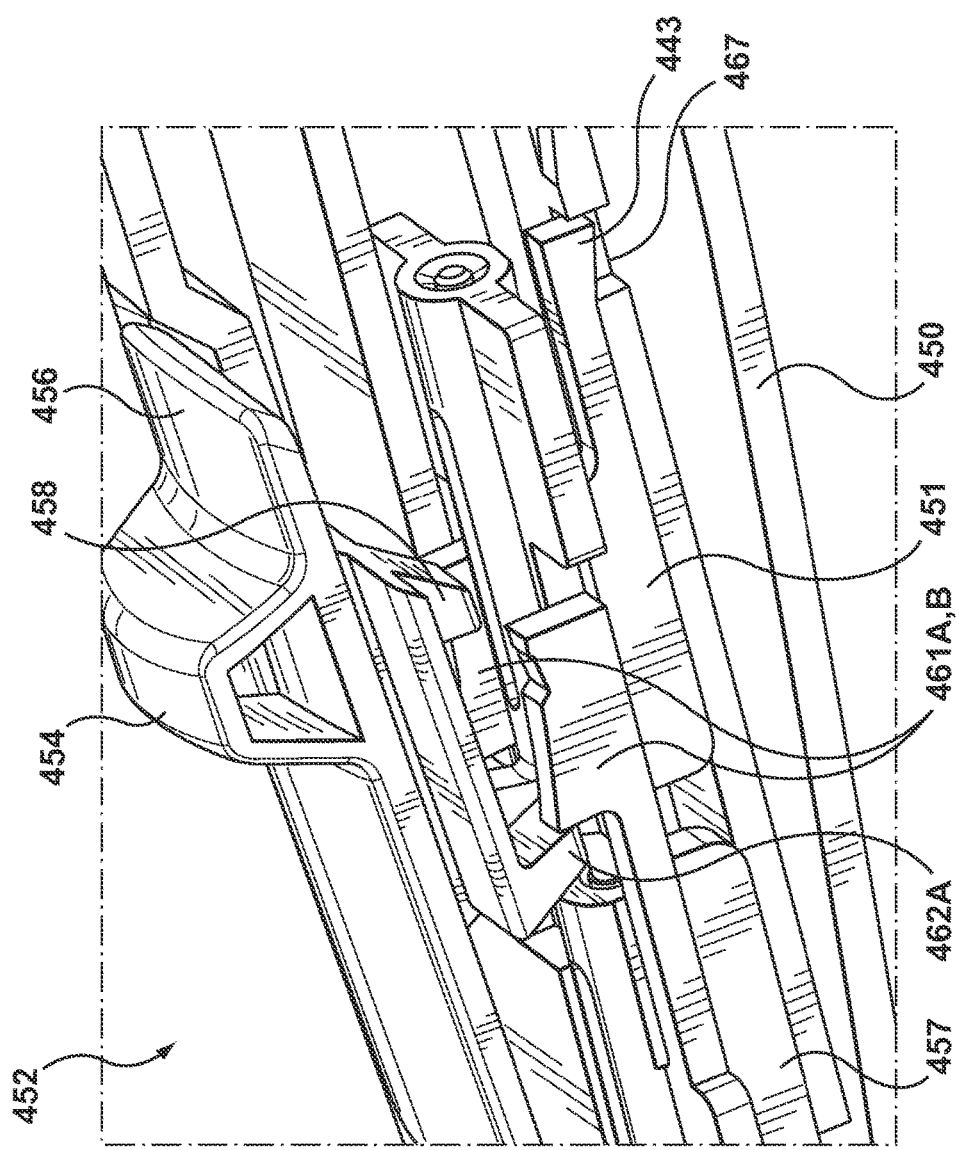

Slider 454 is proximally retracted to the position shown in FIGS. 19 and 20, in which proximal end 456 thereof abuts against proximal surface 447 of recess 449 within handle 450 and distal end 478 of intermediate shaft 474 is positioned proximal to proximal ends of plug 408 and sleeve 406. FIG. 19 is an enlarged view of only the distal end of the suture connector placement device while FIG. 20 illustrates handle 450 of the suture connector placement device as well. FIG. 20A is a perspective view of a portion of handle 450. With intermediate shaft 474 removed from between plug 408 and sleeve 406, sleeve 406 is released to contact or clamp onto plug 408 thereby securing suture portions 1112 between the sleeve and the plug. Stated another way, when intermediate shaft 474 is retracted, sleeve 406 is no longer in contact with the outer surface of intermediate sleeve 474 and sleeve 406 thereby releases onto plug 408, thereby enveloping, covering, wrapping around or otherwise surrounding plug 408. When sleeve 406 is released onto plug 408, radial protrusions 409 of plug 408 may compress or flatten due to the contact between the sleeve and the plug, thereby ensuring an interference or press fit there-between. In an embodiment hereof, sleeve 406 is formed from a resilient or elastic material such as but not limited to an elastomer. In an embodiment hereof, sleeve 406 is formed from silicone. In the loaded configuration of suture connector 404 discussed above, sleeve 406 is stretched or expanded over intermediate shaft 474 and when intermediate shaft 474 is retracted, sleeve 406 resiliently contracts or compresses onto plug 408. At this point in the method of use, slider 454 and intermediate shaft 474 are each in a retracted position and suture connector 404 is in a fully deployed configuration since plug 408 is in contact with sleeve 406 with suture portions 1112 sandwiched there-between. Stated another way, when sleeve 406 is released onto plug 408, suture portions 1112 extending between the plug and the sleeve are thereby secured or fixed relative to each other within the formed suture connector 404.

In another embodiment hereof, in order to ensure contact between plug 408 and sleeve 406 of suture connector 404 upon retraction of intermediate shaft 474, the plug of the suture connector may be formed from a resilient or elastic material in addition to or as an alternative to forming the sleeve of a resilient material. More particularly, plug 408 may be formed from a resilient material that is slightly compressed into intermediate shaft 474 such that plug 408 is still moveable relative to or slideable within the intermediate shaft. After plug 408 has been longitudinally positioned within sleeve 406 and intermediate shaft 474 is retracted, plug 408 may resiliently radially expand into contact with sleeve 406 thereby securing suture portions 1112 between the sleeve and the plug.

Upon retraction of intermediate shaft 474, suture connector 404 is still disposed within the outer shaft of the suture connector placement device 402 but has been decoupled therefrom such that the suture connector remains in situ when the suture connector placement device is proximally retracted. Accordingly, when suture connector placement device 402 is proximally retracted and removed from the patient, suture connector 404 remains in situ with suture portions 1112 secured therein. Since it is not required to push or eject suture connector 404 from suture connector placement device 402, suture connector 404 may be formed from less rigid or less stiff materials than would otherwise be required if suture connector 404 had to be pushed or ejected from suture connector placement device 402. In an embodiment hereof, sleeve 406 is formed from silicone and plug 408 is formed from collagen. Such materials are very biocompatible and may be preferred over rigid or stiff materials that would otherwise be required if suture connector 404 was to be pushed or ejected from suture connector placement device 402. In another embodiment hereof, sleeve 406 and plug 408 may be formed from more rigid biocompatible materials such as but not limited to polypropylene.

In addition to the material of suture connector 404, other advantages flow or result from the fact sleeve 406 is resiliently released onto plug 408 via retraction of the intermediate shaft and there is no requirement to push or eject the formed connector out of the device. More particularly, pushing or ejecting the formed connector out of the suture connector placement device may result in pushing the suture connector through arteriotomy $V_A$ in the vessel wall $V_W$ of a vessel. If inadvertently pushed through the arteriotomy, suture connector 404 may contact and damage the inner vessel wall opposite the incision/arteriotomy. Further, if inadvertently pushed through the arteriotomy, suture connector 404 may not result in full closure and hemostasis at the treatment site.

Figure 21:
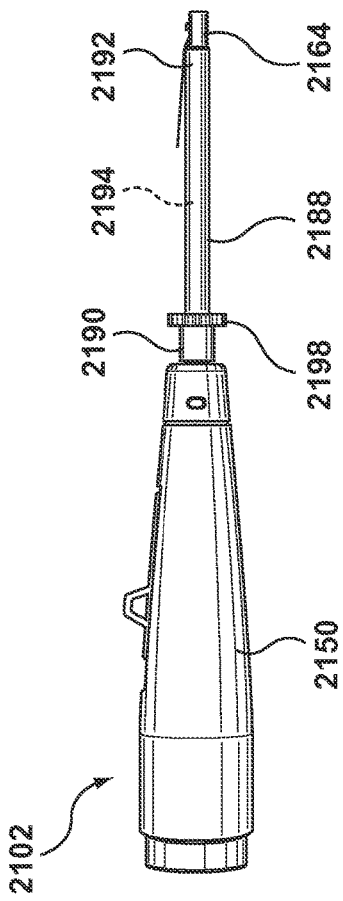
FIG. 21 is a side view of a suture connector placement device for positioning a suture connector in situ according to another embodiment hereof, wherein the suture connector placement device includes an outermost shaft having a cutting surface at its distal end.
Figure 23:
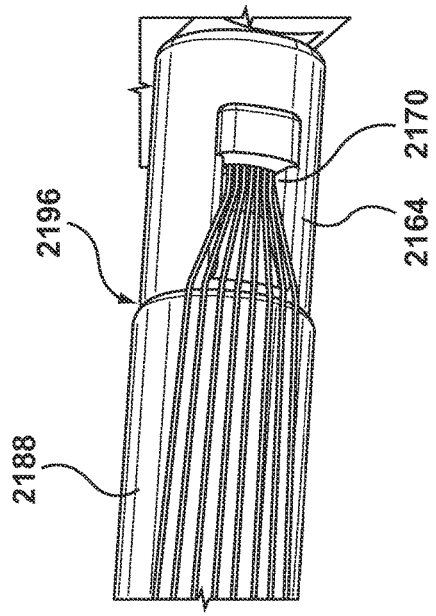
FIG. 23 is an enlarged view of a portion of FIG. 22.
Figure 22:
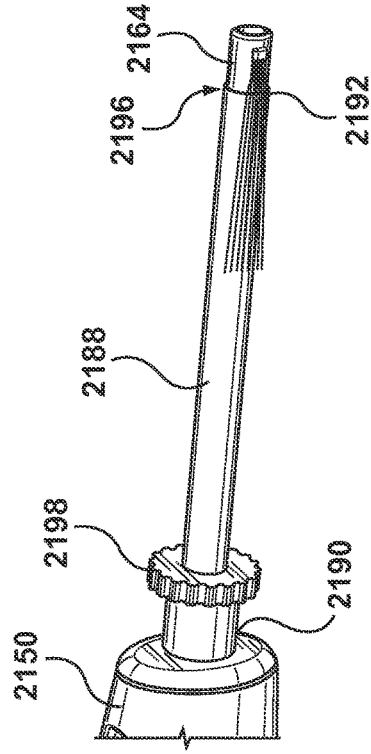
FIG. 22 is a perspective view of a distal portion of the suture connector placement device of FIG. 21.

FIGS. 21, 22, and 23 illustrate another embodiment of a suture connector placement device 2101. Suture connector placement device 2101 includes a handle 2150 and outer shaft 2164 and is similar to connector placement 402 described above, except that suture connector placement device 2101 further includes an outermost shaft 2188 rotatably disposed over outer shaft 2164. Outermost shaft 2188 is a tubular component having a proximal end 2190 disposed adjacent to handle 2150 and a distal end 2192 disposed proximal to side port or opening 2170 of outer shaft 2164. Outermost shaft 2188 defines a lumen 2194 (shown in phantom in FIG. 21) there-through. Distal end 2192 of outermost shaft 2188 includes a cutting surface 2196 that is operable to sever a suture. The proximal end 2190 of outermost shaft 2188 includes a wheel 2198 for rotating the outer shaft relative to outer shaft 2164. After a suture connector is formed, i.e., after a plug is in contact with a sleeve with suture portions sandwiched there-between, a user may rotate outermost shaft 2188 relative to outer shaft 2164 via wheel 2188 and cutting surface 2196 severs the suture portions adjacent to where they extend out of side port 2170 of outer shaft 2164. In another embodiment, the suture portions may be cut manually.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A system for forming a suture connector in situ comprising:
 a suture connector placement device including,
  a handle having an actuating mechanism,
  an outer shaft defining a lumen from a proximal end to a distal end thereof, wherein the proximal end of the outer shaft is coupled to the handle and wherein the outer shaft includes a side opening adjacent to the distal end thereof,
  an intermediate shaft defining a lumen from a proximal end to a distal end thereof, wherein the intermediate shaft is slidingly disposed within the lumen of the outer shaft with the proximal end of the intermediate shaft being coupled to the actuating mechanism of the handle,
  a push rod slidingly disposed within the lumen of the intermediate shaft, wherein the proximal end of the push rod is coupled to the actuating mechanism of the handle; and
 a suture connector including a sleeve and a plug,
 wherein when the suture connector is in a loaded configuration within the suture connector placement device, the sleeve of the suture connector is concentrically disposed over an outer surface of the intermediate shaft within the lumen of the outer shaft adjacent to the distal end thereof and the plug of the suture connector is slidably disposed within the lumen of the intermediate shaft proximal of the sleeve.

2. The system of claim 1, wherein the actuating mechanism permits distal advancement of the push rod relative to the intermediate shaft to slide the plug within the lumen of the intermediate shaft until the plug is longitudinally positioned within the sleeve thereon.

3. system of claim 2, wherein the actuating mechanism permits proximal retraction of the intermediate shaft relative to the push rod to free the sleeve from contact with the outer surface of the intermediate sleeve such that the sleeve releases onto the plug.

4. The system of claim 3, wherein the actuating mechanism permits distal advancement of the push rod relative to the intermediate shaft while the intermediate shaft is held stationary and the actuating mechanism permits proximal retraction of the intermediate shaft relative to the push rod while the push rod is held stationary.

5. The system of claim 4, wherein the actuating mechanism includes a slider having a first knob at its proximal end configured to engage the proximal end of the push rod via a first coupler and at least a second knob at this distal end configured to engage the proximal end of the intermediate shaft via a second coupler.

6. The system of claim 1, wherein the distal end of the outer shaft is configured to abut against an outer surface of a vessel wall.

7. The system of claim 1, further comprising:
 an outermost shaft rotatably disposed over the outer shaft, the outermost shaft having a distal end disposed proximal to the side opening of the outer shaft, wherein the distal end of the outermost shaft includes a cutting surface operable to sever at least one suture portion.

8. The system of claim 7, wherein a proximal end of the outermost shaft includes a wheel for rotating the outermost shaft relative to the outer shaft.

9. The system of claim 1, wherein the sleeve is formed from silicone.

10. The system of claim 9, wherein the plug is formed from collagen.

11. A system for forming a suture connector in situ comprising:
 a suture connector placement device including,
  a handle having an actuating mechanism,
  an outer shaft defining a lumen from a proximal end to a distal end thereof, wherein the proximal end of the outer shaft is coupled to the handle and wherein the outer shaft includes a side opening adjacent to the distal end thereof, the distal end of the outer shaft being configured to abut against an outer surface of a vessel wall,
  an intermediate shaft defining a lumen from a proximal end to a distal end thereof, wherein the intermediate shaft is slidingly disposed within the lumen of the outer shaft with the proximal end of the intermediate shaft being coupled to the actuating mechanism of the handle, the actuating mechanism being configured to proximally retract the intermediate shaft,
  a push rod slidingly disposed within the lumen of the intermediate shaft, wherein the proximal end of the push rod is coupled to the actuating mechanism of the handle, the actuating mechanism being configured to distally advance the push rod; and
 a suture connector including a sleeve formed of a resilient material and a plug,
 wherein when the suture connector is in a loaded configuration within the suture connector placement device, the sleeve of the suture connector is disposed on an outer surface of the intermediate shaft within the lumen of the outer shaft adjacent to the distal end thereof and the plug of the suture connector is slidably disposed within the lumen of the intermediate shaft proximal of the sleeve, and
 wherein distal advancement of the push rod moves the plug to longitudinally position the plug within the sleeve and proximal retraction of the intermediate shaft releases the sleeve onto the plug.

12. The system of claim 11, the suture connector placement device further including an outermost shaft rotatably disposed over the outer shaft, the outermost shaft having a distal end disposed proximal to the side opening of the outer shaft, wherein the distal end of the outermost shaft includes a cutting surface operable to sever the at least one suture portion.

13. The system of claim 12, wherein a proximal end of the outermost shaft includes a wheel for rotating the outermost shaft relative to the outer shaft.

14. The system of claim 11, wherein the sleeve is formed from silicone and the plug is formed from collagen.

15. The system of claim 11, wherein the actuating mechanism includes a slider having a first knob at its proximal end configured to engage the proximal end of the push rod via a first coupler and at least a second knob at this distal end configured to engage the proximal end of the intermediate shaft via a second coupler.

16. A system for forming a suture connector in situ comprising:
 a suture connector placement device including, a handle having an actuating mechanism, an outer shaft defining a lumen from a proximal end to a distal end thereof, wherein the proximal end of the outer shaft is coupled to the handle and wherein the outer shaft includes a side opening adjacent to the distal end thereof, an intermediate shaft defining a lumen from a proximal end to a distal end thereof, wherein the intermediate shaft is slidingly disposed within the lumen of the outer shaft with the proximal end of the intermediate shaft being coupled to the actuating mechanism of the handle, a push rod slidingly disposed within the lumen of the intermediate shaft, wherein the proximal end of the push rod is coupled to the actuating mechanism of the handle; and a suture connector including a sleeve and a plug, wherein when the suture connector is in a loaded configuration within the suture connector placement device, the sleeve of the suture connector is radially disposed between the outer shaft and the intermediate shaft adjacent to the distal end of the outer shaft and the plug of the suture connector is slidably disposed within the lumen of the intermediate shaft proximal of the sleeve.

17. The system of claim 16, wherein the actuating mechanism permits distal advancement of the push rod relative to the intermediate shaft to slide the plug within the lumen of the intermediate shaft until the plug is longitudinally positioned within the sleeve thereon and wherein the actuating mechanism permits proximal retraction of the intermediate shaft relative to the push rod to free the sleeve from contact with an outer surface of the intermediate sleeve such that the sleeve releases onto the plug.

18. The system of claim 16, wherein the distal end of the outer shaft is configured to abut against an outer surface of a vessel wall.

19. The system of claim 16, further comprising:
an outermost shaft rotatably disposed over the outer shaft, the outermost shaft having a distal end disposed proximal to the side opening of the outer shaft, wherein the distal end of the outermost shaft includes a cutting surface operable to sever at least one suture portion.

20. The system of claim 16, wherein the sleeve is formed from silicone and the plug is formed from collagen.

* * * * *